US009402892B2

(12) United States Patent
MacAdam

(10) Patent No.: US 9,402,892 B2
(45) Date of Patent: Aug. 2, 2016

(54) INACTIVATED POLIOVACCINE

(75) Inventor: Andrew MacAdam, Potters Bar (GB)

(73) Assignee: The Secretary of State for Health, London (GB)

( * ) Notice: Subject to any disclaimer, the term of this patent is extended or adjusted under 35 U.S.C. 154(b) by 0 days.

(21) Appl. No.: 13/977,399

(22) PCT Filed: Dec. 29, 2011

(86) PCT No.: PCT/GB2011/001779
§ 371 (c)(1),
(2), (4) Date: Sep. 10, 2013

(87) PCT Pub. No.: WO2012/090000
PCT Pub. Date: Jul. 5, 2012

(65) Prior Publication Data
US 2013/0344108 A1 Dec. 26, 2013

(30) Foreign Application Priority Data
Dec. 29, 2010 (GB) .................................. 1022077.0

(51) Int. Cl.
| | |
|---|---|
| *C07K 14/105* | (2006.01) |
| *C07K 14/085* | (2006.01) |
| *A61K 39/13* | (2006.01) |
| *A61K 39/125* | (2006.01) |
| *C12N 15/43* | (2006.01) |
| *C12N 15/41* | (2006.01) |
| *C12N 7/00* | (2006.01) |
| *A61K 39/12* | (2006.01) |
| *A61K 39/00* | (2006.01) |

(52) U.S. Cl.
CPC .................. *A61K 39/13* (2013.01); *A61K 39/12* (2013.01); *A61K 39/125* (2013.01); *C12N 7/00* (2013.01); *A61K 2039/5252* (2013.01); *A61K 2039/5254* (2013.01); *A61K 2039/5256* (2013.01); *C12N 2770/32011* (2013.01); *C12N 2770/32611* (2013.01); *C12N 2770/32621* (2013.01); *C12N 2770/32634* (2013.01); *C12N 2770/32662* (2013.01); *G01N 2333/085* (2013.01)

(58) Field of Classification Search
CPC ............ A61K 39/12; A61K 2039/525; A61K 2039/5252; A61K 39/13; C12N 7/00; C12N 15/86; C12N 15/111; C12N 15/113; C12N 2310/531; C12N 2770/32021; C12N 2830/00; C12N 2770/32022; C12N 2770/32034
See application file for complete search history.

(56) References Cited

U.S. PATENT DOCUMENTS

| | | | | |
|---|---|---|---|---|
| 8,557,252 | B2 * | 10/2013 | MacAdam | ................ 424/217.1 |
| 2010/0158945 | A1 * | 6/2010 | MacAdam | ................ 424/217.1 |
| 2014/0112952 | A1 * | 4/2014 | MacAdam | ................ 424/217.1 |

FOREIGN PATENT DOCUMENTS

| | | |
|---|---|---|
| EP | 0 383 433 A1 | 8/1990 |
| WO | 98/41619 A1 | 9/1998 |
| WO | 0007622 A1 | 2/2000 |
| WO | 2008017870 A1 | 2/2008 |

OTHER PUBLICATIONS

Kohara M, Abe S, Komatsu T, Tago K, Arita M, Nomoto A. A recombinant virus between the Sabin 1 and Sabin 3 vaccine strains of poliovirus as a possible candidate for a new type 3 poliovirus live vaccine strain. J Virol. Aug. 1988;62(8):2828-35.*

Chumakov, K., et al., "Inactivated Vaccines Based on Alternatives to Wild-Type Seed Virus," Developments in Biologicals (Basel) 105:171-177, 2001.

Combelas, N., et al., "Recombination Between Poliovirus and Coxsackie A Viruses of Species C: A Model of Viral Genetic Plasticity and Emergence," Viruses 3(8):1460-1484, Aug. 2011.

Dragunsky, E., et al., "Transgenic Mice as an Alternative to Monkeys for Neurovirulence Testing of Live Oral Poliovirus Vaccine: Validation by a WHO Collaborative Study," Bulletin of the World Health Organization 81(4):251-260, May 2003.

Evans, D.M., et al., "Increased Neurovirulence Associated With a Single Nucleotide Change in a Noncoding Region of the Sabin Type 3 Poliovacine Genome," Nature 314(6011):548-550, Apr. 1985.

Georgescu, M.M., et al., "Mapping of Mutations Contributing to the Temperature Sensitivity of the Sabin 1 Vaccine Strain of Poliovirus," Journal of Virology 69(9):5278-5286, Sep. 1995.

Gutiérrez, A.L., et al., "Attenuating Mutations in the Poliovirus 5' Untranslated Region Alter Its Interaction With Polypyrimidine Tract-Binding Protein," Journal of Virology 71(5):3826-3833, May 1997.

Holland, J.J., et al., "RNA Virus Populations as Quasispecies," in J.J. Holland (ed.), "Genetic Diversity of RNA Viruses: Current Topics in Microbiology and Immunology," Springer, Berlin, 1992, vol. 176, Chap. 1, pp. 1-20.

La Monica, N., et al., "Mapping of Sequences Required for Mouse Neurovirulence of Poliovirus Type 2 Lansing," Journal of Virology 57(2):515-525, Feb. 1986.

MacAdam, A.J., et al., "The 5' Noncoding Region and Virulence of Poliovirus Vaccine Strains," Trends in Microbiology 2(11):449-454, Nov. 1994.

MacAdam, A.J., et al., "The 5' Noncoding Region of the Type 2 Poliovirus Vaccine Strain Contains Determinants of Attenuation and Temperature Sensitivity," Virology 181(2):451-458, Apr. 1991.

(Continued)

*Primary Examiner* — Rachel B Gill
(74) *Attorney, Agent, or Firm* — Christensen O'Connor Johnson Kindness PLLC

(57) ABSTRACT

The invention provides an attenuated polio virus having a 5' non-coding region consisting of the 5' non-coding region of Sabin 3, modified so that it does not have a base pair mismatch in stem (a) or (b) of domain V, wherein seven or eight of the base pairs in stems (a) and (b) are U-A or A-U base pairs; and a capsid protein from the Sabin 1, Mahoney, MEF or Saukett strain.

13 Claims, 4 Drawing Sheets

(56) References Cited

OTHER PUBLICATIONS

MacAdam, A.J., et al., "Correlation of RNA Secondary Structure and Attenuation of Sabin Vaccine Strains of Poliovirus in Tissue Culture," Virology 189(2):415-422, Aug. 1992.

MacAdam, A.J., et al., "Live-Attenuated Strains of Improved Genetic Stability," Developments in Biologicals (Basel) 105:179-187, 2001.

MacAdam, A.J., et al., "Rational Design of Genetically Stable, Live-Attenuated Poliovirus Vaccines of All Three Serotypes: Relevance to Poliomyelitis Eradication," Journal of Virology 80(17):8653-8663, Sep. 2006.

Nomoto, A., et al., "Complete Nucleotide Sequence of the Attenuated Poliovirus Sabin 1 Strain Genome," Proceedings of the National Academy of Sciences of the USA (PNAS) 79(19):5793-5797, Oct. 1982.

Skinner, M.A., et al., "New Model for the Secondary Structure of the 5' Non-Coding RNA of Poliovirus Is Supported by Biochemical and Genetic Data That Also Show That RNA Secondary Structure Is Important in Neurovirulence," Journal of Molecular Biology 207(2):379-392, May 1989.

Stanway, G., et al., "Comparison of the Complete Nucleotide Sequences of the Genomes of the Neurovirulent Poliovirus P3/Leon/37 and Its Attenuated Sabin Vaccine Derivative P3/Leon 12a1b," Proceedings of the National Academy of Sciences of the USA (PNAS) 81(5):1539-1543, Mar. 1984.

Vignuzzi, M., et al., "Quasispecies Diversity Determines Pathogenesis Through Cooperative Interactions in a Viral Population," Nature 439(7074):344-348, Jan. 2006.

Vignuzzi, M., et al., "Engineering Attenuated Virus Vaccines by Controlling Replication Fidelity," Nature Medicine 14(21):154-161, Feb. 2008.

International Search Report mailed Nov. 28, 2007, issued in related International Application No. PCT/GB2007/003065, filed Aug. 10, 2007, 4 pages.

International Preliminary Report on Patentability and Written Opinion mailed Feb. 10, 2009, issued in related International Application No. PCT/GB2007/003065, filed Aug. 10, 2007, 8 pages.

Almond, J., et al., "Approaches to the Construction of New Candidate Poliovirus Type 3 Vaccine Strains," Developments in Biological Standardization 78:161-169, 1993.

Girard, M., et al., "Potential Use of Poliovirus as a Vector," Biologicals 21(4):371-377, Dec. 1993.

International Preliminary Report on Patentability and Written Opinion mailed Jul. 2, 2013, issued in corresponding International Application No. PCT/GB2011/001779, filed Dec. 29, 2011, 7 pages.

International Search Report mailed Apr. 4, 2012, issued in corresponding International Application No. PCT/GB2011/001779, filed Dec. 29, 2011, 3 pages.

\* cited by examiner

INACTIVATED POLIOVACCINE

FIELD OF THE INVENTION

This invention relates to inactivated poliovaccines. In particular, the invention relates to inactivated poliovaccines, attenuated polioviruses used in the production of inactivated poliovaccines and to the preparation of such inactivated poliovaccines.

BACKGROUND OF THE INVENTION

The global polio eradication initiative of the World Health Organisation (WHO) has made great progress. The main tool used in the program has been the live attenuated oral polio vaccine. This live attenuated vaccine has been known for many years to cause vaccine associated poliomyelitis in a small proportion of recipients or their contacts, and more recently to be able to revert to a transmissible phenotype, causing outbreaks in several parts of the world where vaccine programs have become less vigorous as polio has disappeared. Prolonged excretion of vaccine-derived polioviruses by some immunodeficient patients has also been well documented. The use of the oral polio vaccine and its ability to alter its phenotype is therefore an issue in the eradication of polio worldwide.

It would be extremely unwise to stop vaccination immediately the last wild type virus is believed to have been isolated because wild type virus may be circulating undetected due to poor surveillance in some areas. Also, immunodeficient individuals may continue to excrete virus for a very long time after vaccination and could be a source for re-emergence. Further, there may still be outbreaks caused by the oral vaccine from the last rounds of its use.

Vaccination and surveillance must therefore continue for some time after eradication of the wild type virus is declared. This requires the use of poliovirus in laboratories engaged in surveillance and in vaccine production, which will be chiefly concerned with the manufacture of inactivated poliovaccine (IPV) of the kind developed by Salk.

The Salk vaccine is based on three wild, virulent wild type strains of poliovirus namely the Mahoney (type 1 poliovirus), MEF-1 (type 2 poliovirus), and Saukett (type 3 poliovirus) strains, grown in Vero cells ex vivo (Wood et al, Biologicals 25:59-64, 1997). The wild type polioviruses are then inactivated with formalin to produce the IPV. The wild type strains currently used in IPV production are known to be paralytic in humans and are used in large amounts in IPV production. This presents a serious containment issue, which may not be easy to reconcile with the production scales required for IPV. Some interest has been expressed in using the same strains in the manufacture of inactivated vaccine as are used in the oral vaccine on the grounds that they are attenuated and therefore present less of a hazard should they escape. However, their instability on replication in humans means that they remain hazardous, and their immunogenic properties are different from those of the wild type strains currently used so that a major clinical development program would be required to develop an IPV based on these strains.

The live attenuated poliovirus vaccines developed by Sabin in the 1950s using essentially empirical procedures have been used throughout the world as live oral poliovaccines. Over the past several years, scientists have employed a number of molecular biological techniques in an attempt to elucidate the mechanism by which the neurovirulence of these vaccine strains is reduced. Most of the work has concentrated on serotypes 1 and 3. For both of these the complete nucleotide sequences of the vaccine strains have been compared with those of their neurovirulent progenitors. In the case of poliovirus type 1, the vaccine strain differs from its progenitor at 47 positions in the 7441 base genome (Nomoto et al., Proc. Natl. Acad. Sci. USA 79:5793-5797, 1982). Analogous studies on poliovirus type 3 reveal just 10 nucleotide sequence differences in the 7432 base genome between the vaccine and its progenitor strain (Stanway et al., Proc. Natl. Acad. Sci. USA 81:1539-1543, 1984).

The type 2 strain was developed from a naturally attenuated parent but analysis of a neurovirulent revertant strain, isolated from a case of vaccine-associated poliomyelitis, identified 17 differences from Sabin 2 (Pollard et al., J. Virol. 63: 4949-4951, 1989).

A model for the secondary structure of the 5' non-coding region of the genome of poliovirus type 3 strain has previously been proposed (Skinner et al., J. Mol. Biol. 207: 379-392, 1989). As concerns domain V (nucleotides 471-538), bases at positions 471-473 and 477-483 are paired with bases at positions 538-536 and 534-528 respectively as follows:

```
      471         477         483
  ... U C C ... C C A U G G A ...

... A G G ... G G U G C C U ...
      538         534         528
```

For convenience, the paired regions are termed stem (a) (471-473/538-536) and stem (b) (477-483/534-528). Attenuated polioviruses in which a base pair of stem (a) or stem (b) of domain V is reversed are disclosed in EP-A-0383433. Attenuated polioviruses that do not have a U-G base pair or other base pair mismatch (departure from Watson-Crick base pairing) in stem (a) or (b) of domain V of the 5' non-coding region of the poliovirus genome are described in WO98/41619 and WO 2008/017870. These attenuated polioviruses have substantially the same attenuation as, or greater attenuation than, the parent Sabin vaccine strain (so that they are safe to use) but are much more stable genetically.

SUMMARY OF THE INVENTION

The present inventors have developed intertypic recombinant poliovirus strains for use as IPV seeds. The poliovirus strains of the invention have improved immunogenic properties and enhanced growth capabilities in tissue culture cells. The poliovirus strains of the invention are also attenuated and genetically stable, making them safe for use in IPV production. In particular, the present inventors have surprisingly found that intertypic recombinant polioviruses comprising a genetically modified 5' non-coding region of Sabin 3, capsid proteins from Sabin 1, Mahoney, MEF or Saukett and non-structural coding regions and 3' non-coding regions from Sabin 3 have improved immunogenic properties compared to the Sabin 3 strain with the same genetic modifications in the 5' non-coding region. The poliovirus strains of the invention can be grown in tissue culture and have the necessary immunogenicity to act as IPV seeds, but will not replicate at all in humans should they be exposed even to large amounts.

Accordingly, the present invention provides an attenuated recombinant poliovirus having:

(i) a 5' non-coding region consisting of the 5' non-coding region of Sabin 3, modified so that it does not have a base pair mismatch in stem (a) or (b) of domain V, wherein seven or eight of the base pairs in stems (a) and (b) are U-A or A-U base pairs; and (ii) a capsid protein from the Sabin 1, Mahoney, MEF or Saukett strain.

The invention also provides:
an inactivated poliovirus of the invention for use in a vaccine;
the use of a poliovirus of the invention as an inactivated poliovaccine (IPV) seed;
a vaccine comprising an inactivated poliovirus and a pharmaceutically acceptable carrier or diluent, and optionally an adjuvant;
a method for preparing an inactivated poliovaccine, comprising:
(i) growing a poliovirus according to any one of claims 1 to 7 in cell culture ex vivo;
(ii) inactivating said poliovirus; and
(iii) formulating said inactivated poliovirus with a pharmaceutically acceptable carrier or diluent.

DETAILED DESCRIPTION OF THE INVENTION

Figure 1:
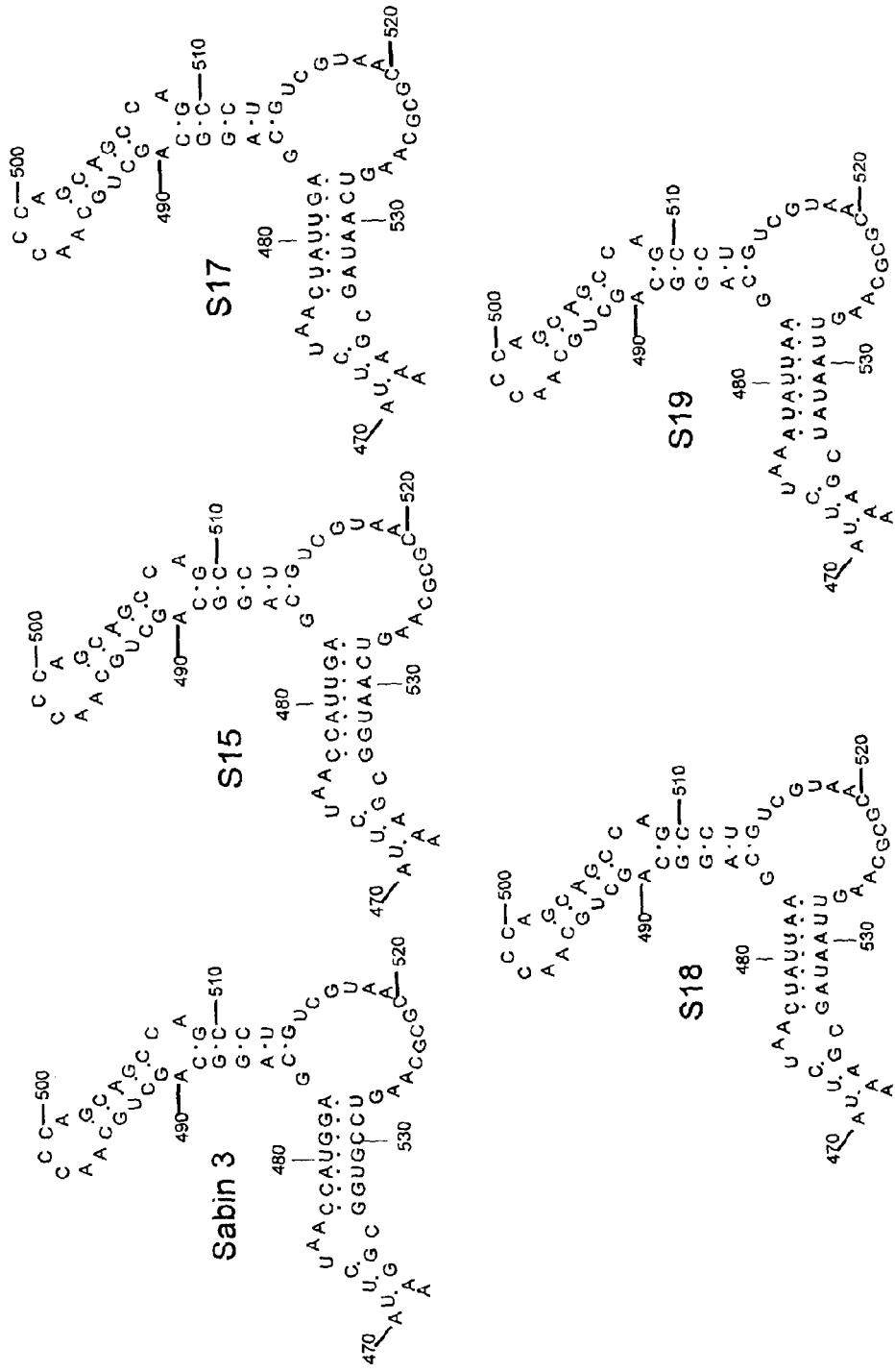
FIG. 1 shows the predicted RNA secondary structure of domain V (nucleotides 471-538) of the type 3 vaccine strain Sabin 3 (SEQ ID NO:13) and strains S15 (SEQ ID NO:14), S17 (SEQ ID NO:15), S18 (SEQ ID NO:1), and S19 (SEQ ID NO:2). Mutations introduced into modified strains are shown in bold.

The poliovirus genome is a single linear RNA molecule that is translated by the host cell as one long polypeptide. The poliovirus RNA comprises a long, highly structured 5' end, which does not code for a polypeptide product and contains six domains, I to VI. Several of these domains (including domain V) together comprise an Internal Ribosome Entry Site (IRES) which determines initiation of translation. The coding region of the poliovirus RNA is divided into two regions, one coding for structural proteins that make up the viral capsid, and the other coding for non-structural proteins such as viral proteases and a viral RNA dependent RNA polymerase. The 3' untranslated region is less complex than the 5' non-coding region.

The present inventors have developed intertypic recombinant strains of poliovirus that possess mutations in domain V of the 5' non-coding region, and so are both attenuated compared to wild type poliovirus strains and genetically stable. The intertypic recombinant poliovirus strains of the invention also have one or more capsid proteins from the Sabin 1, Sabin 2, Sabin 3, Mahoney, MEF or Saukett poliovirus strains. Poliovirus capsid proteins form the protein coat that surrounds the poliovirus particle. These capsid proteins are therefore exposed to the immune system of the host and direct the host's immune response to the poliovirus. Changing the capsid protein of the intertypic recombinant poliovirus allows the immunogenic properties of the poliovirus to be manipulated.

Accordingly, attenuated polioviruses of the invention comprise the 5' non-coding region of Sabin 3, which has been modified so that stems (a) and (b) of domain V do not contain a base pair mismatch and seven or eight of the base pairs in stems (a) and (b) are A-U or U-A base pairs. The attenuated poliovirus of the invention also comprises a capsid protein, such one capsid protein, more than one capsid protein or all structural proteins from the Sabin 1, Sabin 2, Sabin 3, Mahoney, MEF or Saukett strain, preferably from Sabin 1, Mahoney, MEF and/or Saukett and more preferably from Mahoney, MEF and/or Saukett.

Modification of Domain V

The attenuated polioviruses of the invention are genetically stable and safe for use as IPV seeds. This is achieved by weakening the structure of domain V in the 5' non-coding region by replacing GC base pairs with AU base pairs so that two simultaneous mutations are required to regenerate the wild type, and replacing GU base pairs with AU base pairs to prevent reversion to GC by a single mutation and consequent strengthening of the structures. It has been shown that viruses adjusted so that the thermodynamic stability of domain V is the same as that of the Sabin type 3 vaccine strain have the same biological properties but are stable on passage (Macadam et al (2006) 3 Virol. 80(17):8653-63). The attenuated poliovirus of the invention comprises a 5' non-coding region consisting of the 5' non-coding region of Sabin 3, modified so that it does not have a base pair mismatch in stem (a) or (b) of domain V, wherein seven or eight of the base pairs in stems (a) and (b) are U-A or A-U base pairs.

In one preferred embodiment, the attenuated poliovirus of the invention comprises a modified domain V of the 5' non-coding region of Sabin 3 in which a U-A base pair is present at positions 471-538 and 472-537 in stem (a) and at positions 478-533, 480-531 and 481-530 in stem (b) and an A-U base pair is present at positions 479-532 and 482-529 in stem (b). The sequence of the modified V domain may be:

(SEQ ID NO: 1)
AUUCUAACUAUUAAGCAGGCAGCUGCAACCCAGCAGCCAGCCUGUCGUA

ACGCGCAAGUUAAUAGCGAAA.

In another preferred embodiment, the attenuated poliovirus of the invention comprises a modified domain V of the 5' non-coding region of Sabin 3 in which a U-A base pair is present at positions 471-538 and 472-537 in stem (a) and at positions 478-533, 480-531 and 481-530 in stem (b) and an A-U base pair is present at positions 477-534, 479-532 and 482-529 in stem (b). The sequence of the modified V domain may be:

(SEQ ID NO: 2)
AUUCUAAAUAUUAAGCAGGCAGCUGCAACCCAGCAGCCAGCCUGUCGUA

ACGCGCAAGUUAAUAUCGAAA.

Polioviruses of the invention can be correspondingly derived from the sequence of stems (a) and (b) of the Sabin 1 or Sabin 2 polioviruses.

The mutations in the 5' non-coding region of the polioviruses of the invention attenuate the virulence of the viruses and genetically stabilise the viruses, thereby making them less likely to revert to virulence. These mutations thus make the virus safe to produce at a lower containment level than the containment level required for the wild-type viruses currently used to produce inactivated poliovaccines.

Mutations in domain V can be introduced by any of the standard methods of mutagenesis known in the art. A mutation can, for example, be introduced into a strain of a poliovirus, normally a Sabin strain, by site-directed mutagenesis of a copy DNA corresponding to the genomic RNA of a poliovirus. This may be achieved by sub-cloning an appropriate region from an infectious DNA copy of a poliovirus genome into the single strand DNA of a bacteriophage such as M13. Alternatively, a mutated sequence can be synthesised entirely in vitro.

After the introduction of the, or each mutation, the modified sub-cloned copy DNAs are reintroduced into the complete copy DNA from which they were derived. Live virus is recovered from the mutated full length copy DNA by production of a positive sense RNA typically using a T7 promoter to direct transcription in vitro (Van der Werf et al., Proc. Natl. Acad. Sci USA 83:2330-2334, 1986).

The recovered RNA may be applied to tissue cultures using standard techniques (Koch, Curr. Top. Microbiol. Immunol. 61:89-138, 1973). After two to three days of incubation, virus can be recovered from the supernatant of the tissue culture. The level of neurovirulence and thus of attenuation of the modified virus may then be compared with that of the unmodified virus using a standard $LD_{50}$ test in mice that are transgenic for the human poliovirus receptor or the WHO-approved vaccine safety test in monkeys (WHO Tech. Rep. Ser. 687:107-175).

Attenuation due to weakening of domain. V has also been shown to correlate approximately with temperature sensitivity in BGM cells (Macadam et al., Virology 181:451-458, 1991) or in L20B cells (as described for CM-1 cells in Macadam et al., Virology 189:415-422, 1992). The temperature sensitivity of modified virus can thus be determined as a preliminary screen to determine the level of attenuation expected. This can be expressed as the temperature (T) at which the number of plaque forming using (pfu) is reduced by a power of 10 (1.0 $\log_{10}$) from the number obtained at, for example, 33° C. or 35° C. in the same cells. The lower the value of T, the greater the degree of attenuation.

Structural Coding Region

The structural coding region of the poliovirus genome encodes caspid proteins, which form the protective protein coat of the poliovirus particles. The attenuated poliovirus of the invention may comprise one or more capsid protein from the Sabin 1, Sabin 2, Sabin 3, Mahoney, MEF or Saukett strain, preferably from the Mahoney, MEF and/or Saukett strain. In a preferred embodiment, the attenuated poliovirus of the invention comprises all of the capsid proteins of the Sabin 1, Mahoney, MEF or Saukett strain. The poliovirus of the invention may comprise capsid proteins from any combination of the different strains, for example from Mahoney and MEF, from Mahoney and Saukett, from MEF and Saukett or from Mahoney, MEF and Saukett.

Intertypic recombinant strains may be produced by standard techniques known in the art.

Non-Structural Coding Region and 3' Non-Coding Region

The poliovirus of the invention may have a non-structural coding region and a 3' non-coding region from any of the Sabin 1, Sabin 2, Sabin 3, Mahoney, MEF and Saukett strains.

In a preferred embodiment, the attenuated poliovirus of the invention has a non-structural coding region and a 3' non-coding region derived from Sabin 3. Producing polioviruses of the invention on a Sabin 3 backbone strain by exchanging the capsid proteins as a cassette eliminates any possible known or unknown effect of recombination, in vitro or in vivo, between the strains outside the capsid regions. It also makes the construction easier and the properties of the viruses more predictable.

In one embodiment, the attenuated poliovirus of the invention has a non-structural coding region and a 3' non-coding region derived from Sabin 1 or Sabin 2, in particular where the 5' non-coding region is derived from Sabin 1 or Sabin 2.

Mutations in the Protease 2A Gene

An attenuated poliovirus of the invention may comprise a mutation in the protease 2A gene, said mutation being associated with higher yields of immunogenic particles in cell lines of monkey origin, such as Vero cells. Such mutations may be obtained by passaging a poliovirus of the invention in Vero cells or by any standard mutagenic technique.

The mutation in the protease 2A gene is typically one that is obtainable by passaging a poliovirus of the invention in Vero cells. Other mutations in the protease 2A gene that increase the yield of poliovirus in monkey cell lines may also be introduced. The mutation in the protease 2A gene may be introduced by directly mutating an infectious poliovirus clone.

In one embodiment, an attenuated poliovirus of the invention comprises a mutation in the protease 2A gene which does not change residues H20, D38 or C109. In a preferred embodiment, the poliovirus protease 2A gene mutation comprises one of the following amino acid changes: A8V, Y10C, 17CY, N18S, T19C, Y19H, L21R, T23I, E25G, A30P, I33V, W35R, K45E, G48D, E65K, E65V, Y70C, T79A, F80L, Y82H, Y93H, H96Y, S105T, P106S, I122V, V123A, G127R, V131A AND S134T.

The mutations in the protease 2A gene are associated with reduced temperature sensitivity and/or greater fitness in cell lines of monkey origin, such as Vero cells, whilst retaining the degree of attenuation that is observed in corresponding polioviruses that lack the protease 2A mutation.

Thus, the invention also provides a method for producing attenuated polioviruses comprising a mutation in the protease 2A gene comprising passaging a poliovirus of the invention in Vero cells and selecting for polioviruses with a mutation in the protease 2A gene associated with higher yields of immunogenic particles, said selection involving:

(i) sequencing the protease 2A gene and identifying appropriate mutations; or (ii) screening the polioviruses to identify virus particles with an unaltered, or substantially unaltered, degree of attenuation and reduced temperature sensitivity compared to the polioviruses of the invention that have not been passaged in Vero cells.

Temperature-sensitivity assays can, for example, be carried out using Vero cells as described in Macadam et al., Virology 189:415-22, 1992.

Mutations in the protease 2A gene can be introduced by any known methods of introducing mutations in DNA as described above.

Preferably, polioviruses of the invention which are grown in non-human cells, such as Vero cells, in IPV production methods comprise at least one mutation in the protease 2A gene as described herein.

Vaccines

The polioviruses of the invention may be used on a small scale in surveillance activities such as seroprevalence studies and on a massive scale in IPV production. The polioviruses of the invention require minimal containment prior to eradication of poliovirus and, post-eradication containment at category BSL3-polio as required by current WHO guidance for viable strains infectious for humans would not be needed.

The attenuated polioviruses may thus be used as (IPV) seeds. Accordingly, the present invention provides an inactivated attenuated poliovirus of the invention. The invention also provides the use of a poliovirus according to the invention as an IPV seed.

Also provided by the invention is a method for preparing an inactivated poliovaccine, comprising:
(i) growing an attenuated poliovirus according to the invention in cell culture ex vivo;
(ii) inactivating said poliovirus; and
(iii) formulating said inactivated poliovirus with a pharmaceutically acceptable carrier or diluent.

The attenuated poliovirus may be grown in cultured non-human cells such as L20B cells and Vero cells. The attenuated poliovirus may be grown in cultured human cells such as MRC5 and Hep2C cells.

The poliovirus may be inactivated by any suitable method. Typically, methods used to inactivate wild-type poliovirus in the currently used IPVs are employed. For example, the poliovirus may be inactivated by formaldehyde, β-propiolactone or binary ethyleneimine treatment, preferably by formaldehyde treatment.

An attenuated poliovirus according to the invention may be inactivated. The inactivated attenuated poliovirus strains of the invention may be combined with a pharmaceutically acceptable carrier or diluent. Any carrier or diluent conventionally used in inactivated virus preparations, such as IPV preparations, may be employed. The IPV preparation may comprise inactivated polioviruses comprising type 1, type 2 and/or type 3 capsid proteins.

The attenuated inactivated polioviruses of the invention can therefore be used to vaccinate against poliomyelitis in a human patient. Accordingly, the invention provides a method of vaccinating a subject against poliovirus, the method comprising administering to a subject in need thereof an effective amount of an inactivated poliovirus of the invention. An effective amount is an amount sufficient to elicit a protective immune response against poliovirus. For this purpose, they may be administered by any suitable route, such as parenterally. Parenteral administration may be by subcutaneous, intradermal or intramuscular injection. The inactivated polioviruses of the invention may be administered with an adjuvant.

A dose corresponding to the amount administered for a conventional IPV, such as 8 to 40 units of D antigen, may be administered.

The dose of the inactivated intertypic recombinant poliovirus of the invention may be adjusted to achieve the required degree of immunogenicity. For example, when a capsid protein is derived from Sabin 2 or Sabin 3 a higher dose may be used than when the capsid protein is derived from Sabin 1, MEF, Mahoney or Saukett. For example, a dose of from about 16 to about 80 units of D antigen, such as about 30 units of D antigen (for example, 32 units of D antigen) or about 60 units of D antigen (for example, 64 units of D antigen) may be used. Lower doses may be used if the vaccine is administered with an appropriate adjuvant.

The present invention provides a vaccine comprising an inactivated poliovirus of the invention and a pharmaceutically acceptable carrier or diluent. The vaccine may further comprise an adjuvant. The vaccine may comprise one or more different intertypic recombinant poliovirus strain of the invention. For example, the vaccine may comprise a mixture of viruses comprising structural proteins from type 1 and type 2, type 1 and type 3, type 2 and type 3 or type 1, type 2 and type 3 poliovirus strains. Typically the type 1 capsid proteins will be from Sabin 1 or Mahoney, preferably Mahoney, the type 2 capsid protein, from Sabin 2 or MEF, preferably MEF and the type 3 capsid proteins from Sabin 3 or Saukett, preferably Saukett.

In view of the different relative immunogenicities of the type 1, type 2 and type 3 polioviruses of the invention, the vaccine may comprise different amounts of polioviruses containing type 1, type 2 and/or type 3 capsid proteins. For example, a type 1:type 2:type 3 ratio of x:y:z may be used where x<y<z. In one specific example, the ratio may be 30:32:45 units of D antigen.

The inactivated poliovirus of the invention may be administered as a stand-alone poliovaccine or in a combination vaccine containing other components, such as DTP (diptheria, pertussis, tetanus), Hib (Haemophilus influenza type B) or Hepatitis B.

The present invention also provides: the use of an inactivated poliovirus according to the invention in the manufacture of a medicament for use in a method of vaccinating against poliovirus; and an inactivated poliovirus according to the invention for use in a method of vaccinating against poliovirus.

The following Examples illustrate the invention.

EXAMPLES

Example 1

Construction of New Strains

S15, S17, S18 and S19 (Table 1, FIG. 1) are derivatives of the type 3 oral poliovaccine strain Sabin 3. Viruses were constructed and recovered by standard methods. Mutated nucleotides are shown in bold in FIG. 1, otherwise sequences are identical to Sabin 3. Replacement of CG base-pairs by UA or AU base-pairs progressively lowers the thermodynamic stability of domain V; removal of all UG base-pairs makes the structure genetically stable as any single mutation would then weaken the relevant base-pair. Two simultaneous mutations would be required to strengthen the structure as this could only be achieved by changing a UA base-pair to a CG (or GC) base-pair.

Viruses were constructed and recovered by standard methods. More specifically, S17, S18 and S19 were constructed by PCR mutagenesis. For each plasmid, three fragments of the 5' non-coding region of Sabin 3 were amplified by PCR using primers incorporating the necessary sequence changes (as shown in FIG. 1), located at nucleotides (a) 31-50 and 471-489, (b) 471-489 and 522-540 and (c) 522-540 and 755-778. The three overlapping-fragments (a)-(c) were gel-purified, mixed and re-amplified with outer primers then the 747 bp fragment comprising the mutated 5' non-coding region was cloned into pCR2.1 (Invitrogen) and sequenced. MluI-SacI (279-751) fragments with correct sequences were ligated into Sabin 3 clones lacking the SacI-SacI (751-1900) fragment. Full-length infectious clones were generated by addition of a partial SacI/SmaI (2768) fragment.

Figure 2:
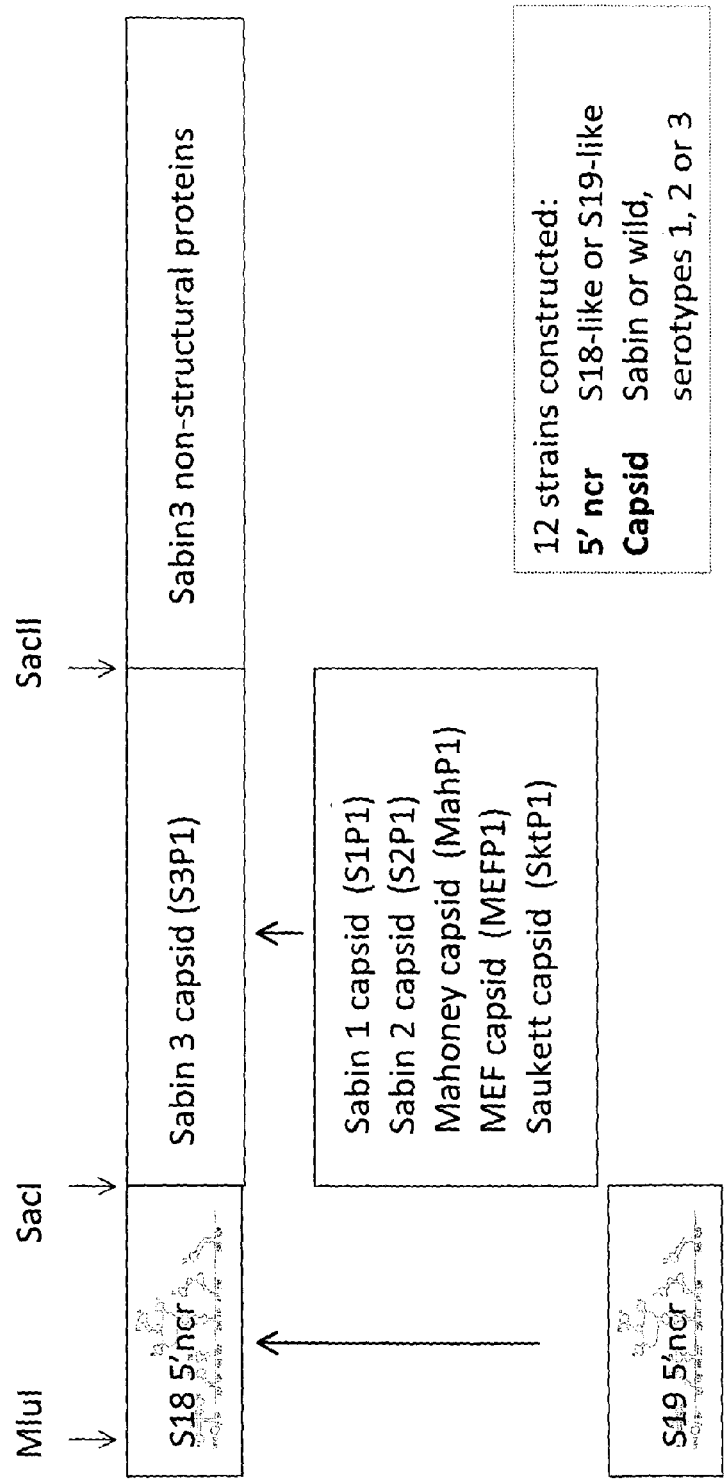
FIG. 2 shows the genomic structures of modified strains based on S18. Unique restriction site, present or introduced into strain S18, are used to interchange domain V and/or capsid protein (P1) coding regions. Virus nomenclature follows the format where "S19/MahP1" denotes a virus with the domain V sequence of S19, the capsid sequence of Mahoney and the non-structural coding region of Sabin 3.

The capsid protein coding regions (P1) of both S18 and S19 were replaced exactly with the P1 regions of the serotype 1 and serotype 2 live-attenuated vaccine strains (Sabin 1 and Sabin 2) or with the P1 regions of the current wild-type IPV seed strains Mahoney (type 1), MEF (type 2) and Saukett (type 3). Capsid sequences were amplified by PCR using RNA from the relevant poliovirus strain as template and primers that incorporated SacI and SacII restriction sites at 5' and 3' ends (FIG. 2) without altering coding sequence.

Sabin 1 and Mahoney P1 regions were amplified using primers:

```
SACI
                                    (SEQ ID NO: 3)
[5'-ATCATAATGGGAGCTCAGGTTTCA-3']
and 2ASAC1(-)
                                    (SEQ ID NO: 4)
[5' TTGTAACCCGCGGTGTACACAGCTTTATTCTGA

TGCCCAAAGCCATATGTGGTCAGAT-3'].
```

The Sabin 2 P1 region was amplified with:

```
SAC2a
                                    (SEQ ID NO: 5)
[5'-ACAATGGGCGCTCAA-3']
and 2ASAC2(-)
                                    (SEQ ID NO: 6)
[5'-TTGTAACCCGCGGTGTACACAGCTTTATTCTGA

TGCCCAAAGCCATAAGTCGTTAATC-3'].
```

The MEF P1 region was amplified with:

```
SAC2b
                                    (SEQ ID NO: 7)
[5'-ACAATGGGAGCTCAA-3']
and 2ASACMEF(-)
                                    (SEQ ID NO: 8)
[5'-TTGTAACCCGCGGTGTACACAGCTTTATTC

TGATGCCCAAAGCCATAGGTTGTCAAGC-3'].
```

The Saukett P1 region was amplified using primers:

```
S3P1
                                    (SEQ TD NO: 9)
[5'-AACTGCGGCCCAGCCGGCCATGGCCGGAGCTC

AAGTATCATCCCAA-3']
and

2ASACSkt(-)
                                    (SEQ ID NO: 10)
[5'-TTGTAACCCGCGGTGTACACAGCTTTATTC

TGATGCCCAAAGCCGTAGGTGGTCAAAC-3'].
```

A SacII restriction site was introduced into S18 by PCR mutagenesis using primers:

```
2ASAC3(+)
                                    (SEQ ID NO: 11)
[5'-GTGTACACCGCGGGTTACAA-3']
and 2ASAC3(-)
                                    (SEQ ID NO: 12)
[5'-TTGTAACCCGCGGTGTACAC-3'].
```

Sequences of DNA fragments comprising copies of all P1 regions were verified before incorporation into full-length genomic plasmids using SacI and SacII restriction sites. Thus twelve final strains were produced (Table 2, FIG. 2) that differed in their domain V sequence (S18-like or S19-like) and their capsid protein coding sequence (Sabin or wild; serotypes 1, 2 or 3). Sequences of 5' non-coding regions of all mutants were confirmed following RNA extraction and RT-PCR.

Viruses were recovered by transfection of HEp2C monolayers with ≥2 µg T7 transcripts (Van der Werf et al, Proc. Natl. Acad. Sci. USA 83:2330-2334, 1986) followed by incubation at 33° C. for 24-48 hours, by which time complete cytopathic effect was apparent.

Example 2

Attenuation Phenotypes and Infectivity

Over the last 15 years the use of transgenic mice expressing the human poliovirus receptor to assess virulence of polioviruses has been established and validated.

Intraspinal inoculation of transgenic mice expressing the poliovirus receptor (TgPVR mice) is a highly sensitive method of measuring infectivity in vivo since virus replication leads to neuronal loss and obvious clinical signs of paralysis. Fewer than ten PFU of wild type viruses is usually sufficient to paralyse 50% of the mice using this route of inoculation (Chumakov et al, Dev. Biol. (Basel) 105:171-177, 2001).

The attenuation phenotypes of the mutated Sabin 3 strains and the intertypic recombinant strains were determined by this standard method. The results are shown in Tables 1 and 2.

TABLE 1

Effect of domain V replacement on attenuation phenotypes

| | TgPVR mice $PD_{50}$ i.s./$\log_{10} CCID_{50}$ |
|---|---|
| Sabin 1 | 2.25 |
| Mahoney | ≤0.7 |
| S15/1 | 2.0 |
| S18/1 | >8.6 (1/16) |
| Sabin 2 | 6.4 |
| Sabin 3 | 3.6 |
| S15 | 3.7 |
| S17 | 7.4 |
| S18 | >8.4 (0/16) |
| S19 | >8.2 (0/16) |
| Leon | 0.7 |

*paralysed/total at highest dose

TABLE 2

Attenuation phenotypes of new vaccine candidate strains

| | TgPVR mice $PD_{50}$ i.s./$\log_{10} CCID_{50}$ |
|---|---|
| S18/S1P1 | >8.25 (0/8)* |
| S18/MahP1 | >8.3 (0/8) |
| S19/S1P1 | >8.15 (0/8) |
| S19/MahP1 | >8.10 (0/8) |
| S18/S2P1 | >8.0 (0/8) |
| S18/MEFP1 | >8.2 (0/8) |
| S19/S2P1 | >8.15 (0/8) |
| S19/MEFP1 | >8.25 (0/8) |
| S18 | >8.4 (0/16) |
| S18/SktP1 | >8.15 (0/8) |
| S19 | >8.2 (0/16) |
| S19/SktP1 | >8.45 (0/8) |

*paralysed/total at highest dose

Using the highly sensitive intraspinal route less than 10 cell culture infectious units of wild type strains Mahoney and Leon were sufficient to paralyse half the mice (Table 1).

Strain S15 was indistinguishable from Sabin 3, as observed in the monkey test (Macadam et al, 2006), and all S18-derived viruses had $PD_{50}$s in excess of $10^8$ $CCID_{50}$ (Tables 1 and 2). These are probably underestimates as they represent the maximum titre practicable in the inoculated dose, which is 5 µl. The effect of 3 CG-UA base-pair exchanges in S19-derived viruses, by extrapolation, is likely to be in excess of a billion-fold reduction in infectivity in this model. These results suggest that viruses based on S18 and S19 would be substantially less infectious for humans than Sabin 3, which has low infectivity unless it reverts in domain V (which these strains cannot).

Example 3

Stability on Passage

To assess stability, viruses were passaged at 37° C. in L20B cells under conditions which rapidly select reversion in domain V of Sabin 3, mimicking selection in the human gut. Under these conditions the domain V sequences of S15 and S16 (phenotypically similar to S15) were completely stable (Macadam et al, 2006). S18- and S19-derived viruses were also stable on passage and have the advantage of additional non-revertible paired mutations. The same was true in Vero cells but selection of reversion in domain V of Sabin 3 occurred at a slower rate.

All Vero selected viruses had a mutation in the protease 2A gene and grew at higher temperatures than their parents, to a limited extent. This phenomenon represents an adaptation to monkey cells and is not seen in cells of human or mouse origin. These mutations appear to have no effect on phenotypes in vivo (Table 3). The $PD_{50}$s of one of the viruses after 10 passes in Vero cells at 37° C., and three of the plaques selected at 37° C. were indistinguishable from those of their parent, S18. Similarly, the presence of the N18S mutation in 2A had no effect on the attenuation of phenotypes of the S19-IPV strains with wild-type capsids (Table 4). At the highest dose administered intraspinally there was no clinical disease in any of the mice. A similar result was previously obtained in the monkey model of poliomyelitis. Two different 2A mutations that suppressed the temperature-sensitive phenotype of Sabin 2, caused by the attenuating mutation at 481 in domain V, did not affect attenuation (Rowe et al.; Virology 269:284-293, 2000).

TABLE 3

Attenuation phenotypes of S18 2A mutants in vivo

| | TgPVR mice $PD_{50}$ i.s./$\log_{10}$ $CCID_{50}$ |
|---|---|
| S18 | >8.4 (0/8)* |
| S18 p10V | >8.2 (0/8)* |
| S18/2A-V123A | >7.9 (0/8)* |
| S18/2A-G127R | >7.9 (0/8)* |
| S18/2A-Y82H | >7.8 (0/8)* |

*paralysed/total at highest dose

TABLE 4

Attenuation phenotypes of S19 $2A^{pro}$ mutants

| | TgPVR mice $PD_{50}$ i.s./$\log_{10}$ $CCID_{50}$ |
|---|---|
| S19/MahP1/2A-N18S | >7.7 (0/8)* |
| S19/MEFP1/2A-N18S | >7.9 (0/8)* |
| S19/MEF2P1/2A-N18S | >7.5 (0/8)* |
| S19/SktP1/2A-N18S | >7.0 (0/8)* |

*paralysed/total at highest dose

Example 4

Growth Properties in Cell Culture

Figure 3:
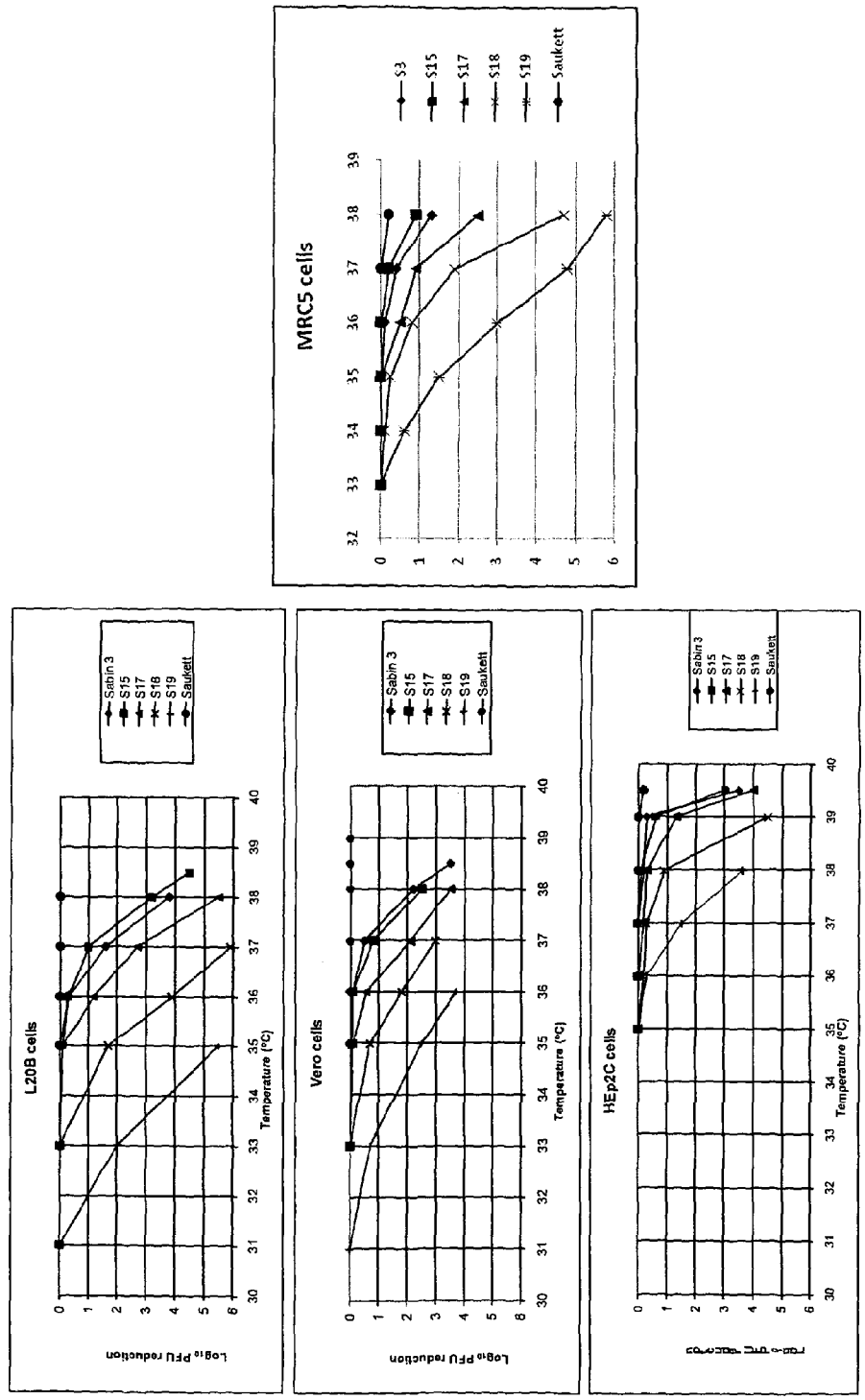
FIG. 3 illustrates the temperature sensitivity of type 3 strains in different cells. Viruses were assayed by plaque-formation at different temperatures in L20B cells, Vero, MRC5 and Hep2C cells and results were plotted on graphs showing the reduction in PFU at each temperature compared to PFU at 31° C.

In cell culture, progressive weakening of domain V RNA secondary structure progressively lowered the upper limit of temperatures at which the virus was able to replicate (FIG. 3). The actual limits depended on the cell substrate used with Hep2C cells being most permissive, L20B cells the least and Vero cells intermediate. MRC5 cells are also intermediate but more permissive than Vero cells.

Figure 4:
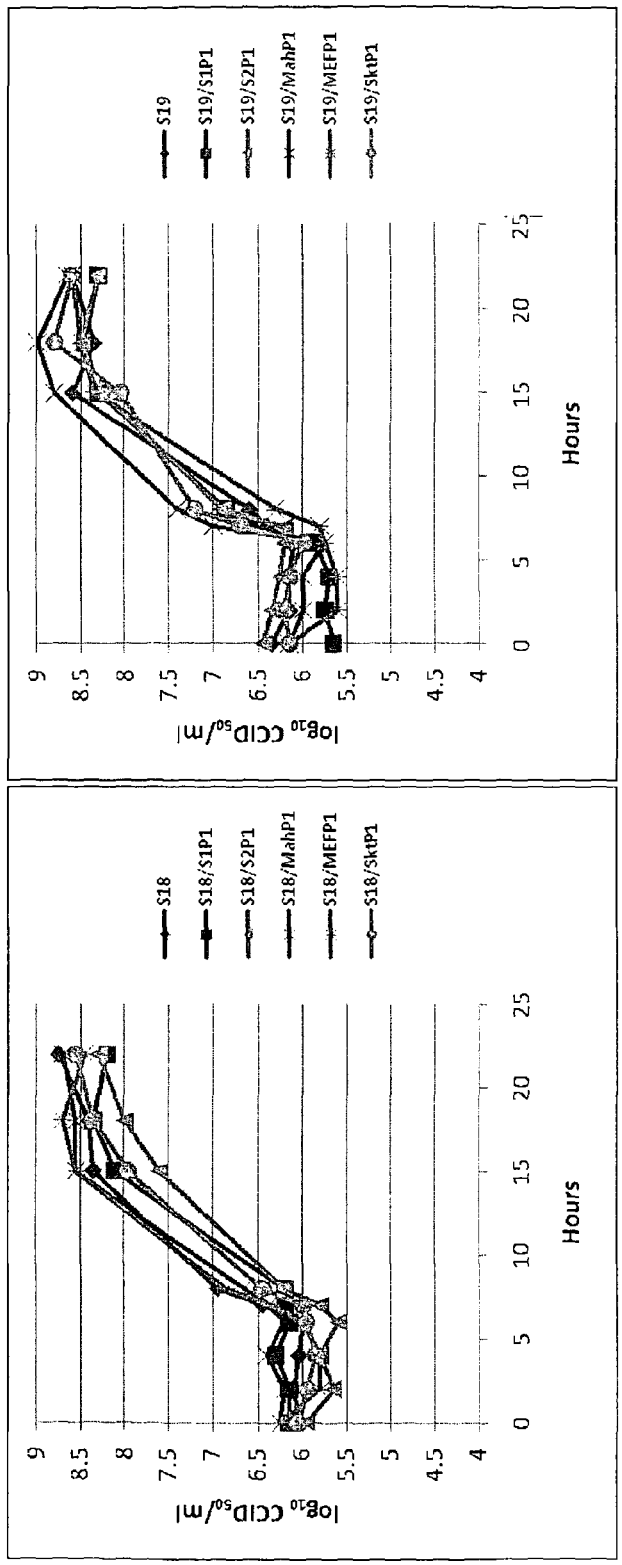
FIG. 4 shows one-step growth in MRC5 cells at 33° C. Replicate cell sheets were synchronously infected with type 3 viruses, incubated at 33° C., then harvested at different times and virus titres determined.

The kinetics of growth and yield of all the strains were similar in MRC5 cells at 33° C., producing yields as high as wild type viruses ($10^8$-$10^9$ $TCID_{50}$/ml) within 24 hours (FIG. 4). MRC5 cells are validated and licensed for IPV production though not many manufacturers use them, preferring serum-free Vero cell culture on micro-carriers. Initial yields in Vero cells were variable, depending on the source and the passage level of the cells, but were routinely lower than in MRC5 cells. So far, titres of $2\times10^8$/ml have been obtained at 24 hours for S18 viruses and $5\times10^7$/ml for S19 viruses. Nevertheless, our preliminary evidence (below) suggests that D-antigen yields in Vero cells equivalent to those obtained with current wild-type seeds can be obtained.

Example 5

Immunogenicity

The two standard batch release assays for IPV products are the D-antigen ELISA test and the rat immunogenicity test (European Pharmacopoeia-supplement 2001 2000:0214 1289-1293). The ELISA assay uses antibodies specific for native polio virions to measure antigenicity and then potency is expressed by comparison with a standard preparation. For the in vivo assay groups of rats are immunised with four dilutions of vaccine and their sera are tested for the presence of neutralising antibodies. Vaccine potency is calculated by statistical comparison of seroconversion rates for test preparations with those obtained with a standard preparation. Both these assays have been employed to assess the immunogenicity of the new strains described here.

For all the viruses listed in Table 5, high titre stocks of virus were prepared and inactivated with formaldehyde using a scaled down manufacturer's protocol (Martin et al., J. Gen. Vir. 84:17814788, 2003). D-antigen ELISAs were carried out on material before and after inactivation. These data were used to calculate appropriate doses for the in vivo assays which were carried out using vaccine batch release Standard Operating Procedures. Vaccines pass the rat test if 95% confidence limits of potency include the value 1.0; thus all constructs with wild type capsids (and S18/S1P1) were sufficiently immunogenic to be released as IPV.

Poliovirus MEF-1 was isolated in 1942 and contained at least two closely related components; MEF-1 strains currently used by IPV manufacturers also differ at several nucleotide positions (Odoom, J K; PhD Thesis, London School of Hygiene and Tropical Medicine, 2008). The capsid protein amino acid sequence of virus S18/MEFP1 was found to differ from that of the IPV potency reference strain at one position so another version, S18/MEF2P1, was constructed which had the same capsid amino acid sequence as the reference. In rat immunogenicity assays S18/MEF2P1 was indistinguishable from the reference strain having a relative potency of 1.0 (Table 4) whereas the virus S18/MEFP1 had a slightly lower potency. Both strains were sufficiently potent to pass a vaccine batch release test (the CI must include a value of 1.0) but strains with MEF2P1 capsid protein sequences are likely to be preferable for vaccine production.

TABLE 5

Antigenicity and immunogenicity of new strains

|  | $CCID_{50}/D$ Ag unit pre-inactivation ($log_{10}$) | D Ag yield after inactivation (%) | $CCID_{50}/D$ Ag unit post-inactivation ($log_{10}$) | Relative potency in vivo (95% CI) |
|---|---|---|---|---|
| S18/S1P1 | 5.6 | 6 | 6.8 | 1.5 (0.8-3.0) |
| S18/MahP1 | 6.0 | 11 | 7.0 | 1.2 (0.6-2.3) |
| S18/S2P1 | 7.0 | 90 | 7.1 | 0.1 (0.04-0.2) |
| S18/MEFP1* | 7.0 | 91 | 7.1 | 0.5 (0.2-1.0) |
| S18/MEF2P1* |  |  | 7.3 | 1.0 (0.4-2.4) |
| Sabin 3 | 6.9 | 38 | 7.3 | 0.4 (0.2-0.9) |
| S18 | 6.7 | 23 | 7.3 | 0.3 (0.1-0.7) |
| S18/SktP1 | 6.8 | 90 | 6.9 | 1.6 (0.8-3.3) |

*S18/MEFP1 contains a single amino acid difference in the capsid protein region compared to the MEF strain used to make the IPV reference; S18/MEF2P1 is identical in the capsid protein region to the MEF strain used to make the IPV reference.

After statistical analysis, the results showed:
(i) The alterations introduced into domain V had no influence on inactivation, antigenicity or immunogenicity.
(ii) Yields of immunogen in terms of DAgU/initial infectious titre were in line with manufacturers data.
(iii) Strains with wild-type capsid proteins were approximately as immunogenic as the equivalent IPV strain.
(iv) Compared to the relevant wild-type reference strain, the strains with Sabin capsid proteins were slightly more (type 1), much less (type 2) and slightly less (type 3) immunogenic.

Example 6

Growth and Stability in Vero Cells

When S18 and S19 strains of polioviruses are grown in Vero cells, their initial replication is quite slow. Polioviruses with particular mutations in the protease 2A gene grow more efficiently in Vero cells. When many polioviruses are grown in Vero cells they adapt for growth in this cell type, and it is mutations in the protease 2A gene that are responsible for the increased growth efficiency. Versions of the S18 and S19 strains which have a suitable modification introduced into the 2A gene (e.g. the mutation N18S) do not require the adaptation step and replicate efficiently in Vero cells from the start. The effect of a V I23A mutation in the protease 2A gene of Sabin 3, S18 and S19 on growth in Vero cells was demonstrated by infecting Vero cells at a multiplicity of infection of 1.0 and incubating the cells for 48 h at 33° C. Yields were measured by a $CCID_{50}$ assay in Hep2C cells at 33° C. The results are shown in Table 6 below.

TABLE 6

Effect of 2A mutations on yield* in Vero cells

|  | $log_{10}$ $CCID_{50}$/ml + | 2A-V123A |
|---|---|---|
| Sabin 3 | 8.5 | 8.7 |
| S18 | 7.8 | 8.6 |
| S19 | 7.2 | 8.3 |

The S18/MahP1 virus and an equivalent virus with a mutation introduced into the 2A gene, S18/MahP1/2A N18S, were both grown in Vero cells at three different temperatures over 10 passages to determine the stability of the protease 2A gene sequence and of the domain V sequence. As shown in Table 7 below, the domain V sequence and the N18S mutated protease 2A gene sequence were completely stable. The unmutated protease 2A gene sequence picked up mutations which facilitate growth in Vero cells, as expected.

TABLE 7

Sequence stability after 10 passages in Vero cells

|  | Passage temperature | Domain V sequence | $2A^{pro}$ sequence |
|---|---|---|---|
| S18/MahP1 | 33° C. | No changes | Mutations selected* |
|  | 35° C. | No changes | Mutations selected* |
|  | 37° C. | No changes | Mutations selected* |
| S18/MahP1/2A N18S | 33° C. | No changes | No changes |
|  | 35° C. | No changes | No changes |
|  | 37° C. | No changes | No changes |

*L17R, N18S, L21R, P90S, S105T or D138N

The invention claimed is:

1. An attenuated recombinant poliovirus having:
   (i) a 5' non-coding region consisting of the 5' non-coding region of Sabin 3 strain of poliovirus, modified so that it does not have a base pair mismatch in stem (a) or (b) of domain V, wherein seven or eight of the base pairs in stems (a) and (b) are U-A or A-U base pairs, and wherein:
   (a) a U-A base pair is present:
       (I) in stem (a) with nucleotide pairs U471 and A538 and U472 and A537; and
       (II) in stem (b) with nucleotide pairs U478 and A533, U480 and A531, and U481 and A530; and
   (b) an A-U base pair is present:
       (I) in stem (b) with nucleotide pairs A479 and U532 and A482 and U529;
       or
   (c) a U-A base pair is present:
       (I) in stem (a) with nucleotide pairs U471 and A538 and U472 and A537; and
       (II) in stem (b) with nucleotide pairs U478 and A533, U480 and A531, and U481 and A530; and
   (d) an A-U base pair is present in stem (b) with nucleotide pairs A477 and U534, A479 and U532, and A482 and U529;
   (ii) a protease 2A coding region from Sabin 3; and
   (iii) an entire capsid protein coding region P1 from the Sabin 1, Mahoney, MEF, or Saukett strain of poliovirus.

2. The poliovirus according to claim 1, further having a 3' non-coding region derived from Sabin 3.

3. The poliovirus according to claim 1, further comprising a mutation in the protease 2A gene, said mutation being associated with higher yields of immunogenic particles in cells of monkey origin.

4. A method for producing the poliovirus according to claim 3, comprising:
   (i) passaging the poliovirus according to claim 1 in Vero cells to identify viral isolates with higher yields of immunogenic particles;
   (ii) sequencing the protease 2A gene of the isolates from step (i);
   (iii) identifying the poliovirus with appropriate mutations in the protease 2A gene from the isolates identified in step (ii); or
   (iv) screening the poliovirus from step (i) to identify viral isolates with an unaltered degree of attenuation and a reduced temperature sensitivity as compared with poliovirus according to claim 1 that have not been passaged.

5. The poliovirus according to claim 3, wherein the mutation in protease A does not change residues H20, D38, or C109.

6. The poliovirus according to claim 3, wherein the mutation is any one or more of the following amino acid changes: A8V, Y10C, C17Y, N18S, T19C, Y19H, T23I, E25G, A30P, I33V, W35R, K45E, G48D, E65K, E65V, Y70C, T79A, F80L, Y82H, Y93H, H96Y, S105T, P106S, I122V, V123A, G127R, V131A, or S134T.

7. The poliovirus according to claim 1, wherein the poliovirus is inactivated.

8. An immunogenic composition comprising the poliovirus of claim 7.

9. The immunogenic composition of claim 8, further comprising a pharmaceutically acceptable carrier or diluent.

10. A poliovirus according to claim 1, wherein the poliovirus is selected as an inactivated polio vaccine (IPV) seed stock.

11. A method for preparing an inactivated polio immunogenic composition, comprising: (i) growing a poliovirus according to claim 1 in cell culture ex vivo; (ii) inactivating said poliovirus; and (iii) formulating said inactivated poliovirus with a pharmaceutically acceptable carrier or diluent.

12. The method according to claim 11, wherein the poliovirus is grown in non-human cells.

13. A method of inducing an immune response in a subject against poliovirus, the method comprising administering to the subject the poliovirus composition of claim 9.

* * * * *

SEQUENCE LISTING

<160> NUMBER OF SEQ ID NOS: 15

<210> SEQ ID NO 1
<211> LENGTH: 70
<212> TYPE: DNA
<213> ORGANISM: Artificial Sequence
<220> FEATURE:
<223> OTHER INFORMATION: modified domain V of polio virus strain
      Sabin 3 - S18

<400> SEQUENCE: 1
auucuaacua uuaagcaggc agcugcaacc cagcagccag ccugucguaa cgcgcaaguu    60
aauagcgaaa                                                           70

<210> SEQ ID NO 2
<211> LENGTH: 70
<212> TYPE: DNA
<213> ORGANISM: Artificial Sequence
<220> FEATURE:
<223> OTHER INFORMATION: modified domain V of polio virus strain
      Sabin 3 - S19

<400> SEQUENCE: 2
auucuaaaua uuaagcaggc agcugcaacc cagcagccag ccugucguaa cgcgcaaguu    60
aauaucgaaa                                                           70

<210> SEQ ID NO 3
<211> LENGTH: 24
<212> TYPE: DNA
<213> ORGANISM: Artificial Sequence
<220> FEATURE:
<223> OTHER INFORMATION: primer

<400> SEQUENCE: 3
atcataatgg gagctcaggt ttca                                           24

<210> SEQ ID NO 4
<211> LENGTH: 58
<212> TYPE: DNA
<213> ORGANISM: Artificial Sequence
<220> FEATURE:
<223> OTHER INFORMATION: primer

<400> SEQUENCE: 4
ttgtaacccg cggtgtacac agctttattc tgatgcccaa agccatatgt ggtcagat      58

<210> SEQ ID NO 5
<211> LENGTH: 15
<212> TYPE: DNA
<213> ORGANISM: Artificial Sequence
<220> FEATURE:
<223> OTHER INFORMATION: primer

<400> SEQUENCE: 5
acaatgggcg ctcaa                                                     15

<210> SEQ ID NO 6
<211> LENGTH: 58
<212> TYPE: DNA
<213> ORGANISM: Artificial Sequence
<220> FEATURE:
<223> OTHER INFORMATION: primer

<400> SEQUENCE: 6
ttgtaacccg cggtgtacac agctttattc tgatgcccaa agccataagt cgttaatc      58

<210> SEQ ID NO 7
<211> LENGTH: 15
<212> TYPE: DNA
<213> ORGANISM: Artificial Sequence
<220> FEATURE:
<223> OTHER INFORMATION: primer

```
<400> SEQUENCE: 7
acaatgggag ctcaa                                             15

<210> SEQ ID NO 8
<211> LENGTH: 58
<212> TYPE: DNA
<213> ORGANISM: Artificial Sequence
<220> FEATURE:
<223> OTHER INFORMATION: primer

<400> SEQUENCE: 8
ttgtaacccg cggtgtacac agctttattc tgatgcccaa agccataggt tgtcaagc   58

<210> SEQ ID NO 9
<211> LENGTH: 46
<212> TYPE: DNA
<213> ORGANISM: Artificial Sequence
<220> FEATURE:
<223> OTHER INFORMATION: primer

<400> SEQUENCE: 9
aactgcggcc cagccggcca tggccggagc tcaagtatca tcccaa               46

<210> SEQ ID NO 10
<211> LENGTH: 58
<212> TYPE: DNA
<213> ORGANISM: Artificial Sequence
<220> FEATURE:
<223> OTHER INFORMATION: primer

<400> SEQUENCE: 10
ttgtaacccg cggtgtacac agctttattc tgatgcccaa agccgtaggt ggtcaaac   58

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
gtgtacaccg cgggttacaa                                        20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
ttgtaacccg cggtgtacac                                        20

<210> SEQ ID NO 13
<211> LENGTH: 70
<212> TYPE: DNA
<213> ORGANISM: Artificial Sequence
<220> FEATURE:
<223> OTHER INFORMATION: domain V of polio virus strain Sabin 3

<400> SEQUENCE: 13
auucuaacca uggagcaggc agcugcaacc cagcagccag ccugucguaa cgcgcaaguc   60
cguggcggaa                                                   70
```

```
<210> SEQ ID NO 14
<211> LENGTH: 70
<212> TYPE: DNA
<213> ORGANISM: Artificial Sequence
<220> FEATURE:
<223> OTHER INFORMATION: modified domain V of polio virus strain
      Sabin 3 - S15

<400> SEQUENCE: 14
auucuaacca uugagcaggc agcugcaacc cagcagccag ccugucguaa cgcgcaaguc        60
aauggcgaaa                                                              70

<210> SEQ ID NO 15
<211> LENGTH: 70
<212> TYPE: DNA
<213> ORGANISM: Artificial Sequence
<220> FEATURE:
<223> OTHER INFORMATION: modified domain V of polio virus strain
      Sabin 3 - S17

<400> SEQUENCE: 15
auucuaacua uugagcaggc agcugcaacc cagcagccag ccugucguaa cgcgcaaguc        60
aauagcgaaa                                                              70
```